United States Patent [19]

Cramer et al.

[11] 4,224,948
[45] Sep. 30, 1980

[54] WRIST BORNE PULSE METER/CHRONOMETER

[76] Inventors: Frank B. Cramer, 14800 Alexander St., Mission Hills, Calif. 91345; J. Lawrence Semar, 17422 Village Dr., Tustin, Calif. 92680

[21] Appl. No.: 963,278

[22] Filed: Nov. 24, 1978

[51] Int. Cl.³ .............................................. A61B 5/02
[52] U.S. Cl. .................................................... 128/690
[58] Field of Search ............................ 128/687–690, 128/698, 705–706, 708; 324/78 D, 186; 364/701–702, 715–717

[56] References Cited

U.S. PATENT DOCUMENTS

| | | | |
|---|---|---|---|
| 3,807,388 | 4/1974 | Orr et al. ............................ | 128/690 |
| 4,022,192 | 5/1977 | Laukien ............................... | 128/706 |
| 4,034,745 | 7/1977 | Bloom ................................. | 324/78 D |
| 4,063,551 | 12/1977 | Sweeney .............................. | 128/690 |
| 4,093,850 | 6/1978 | Karnowski et al. .................. | 364/701 |
| 4,096,854 | 6/1978 | Perica et al. ......................... | 128/690 |
| 4,163,447 | 8/1979 | Orr ........................................ | 128/690 |

*Primary Examiner*—Robert W. Michell
*Assistant Examiner*—Francis J. Jaworski
*Attorney, Agent, or Firm*—John E. Wagner

[57] ABSTRACT

A combined watch, elapsed time counter and pulse rate meter which is totally portable and worn as an ordinary wristwatch. The timer and pulse rate meter employ the precise timing elements such as a crystal oscillator of the digital watch. Using such precise timing elements, the human's pulse may be measured on a pulse by pulse basis and the instantaneous and average pulse values simultaneously displayed to allow a running comparison and noting of pulse aberrations. A novel pulse detector assembly is located on the inner face of the watch assembly.

15 Claims, 9 Drawing Figures

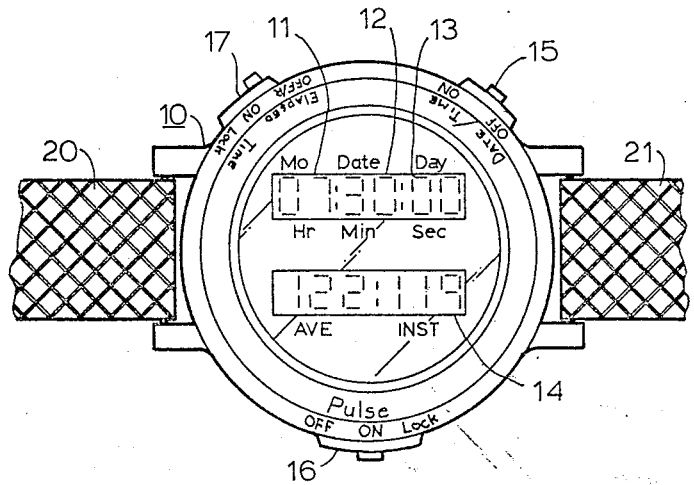
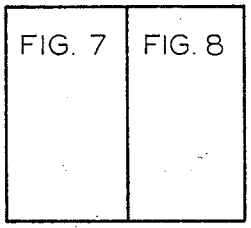
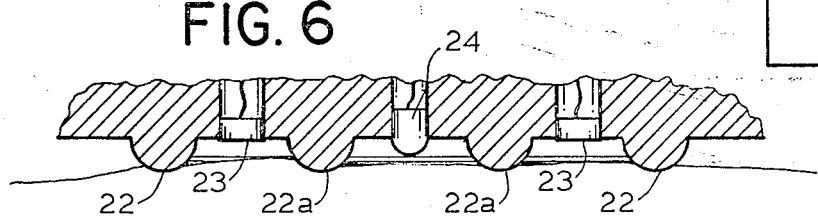
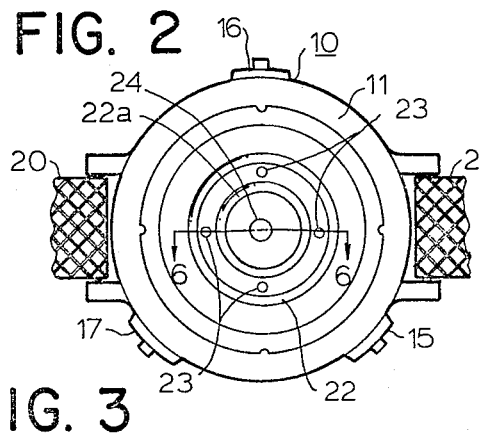
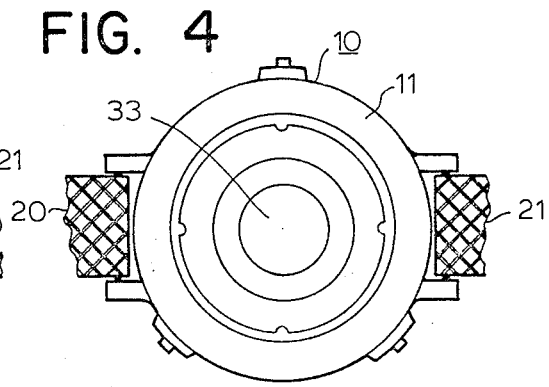
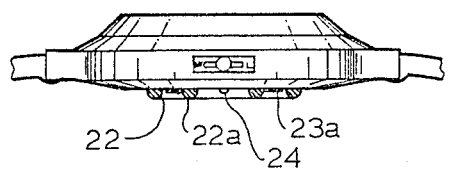
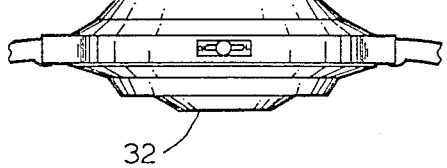

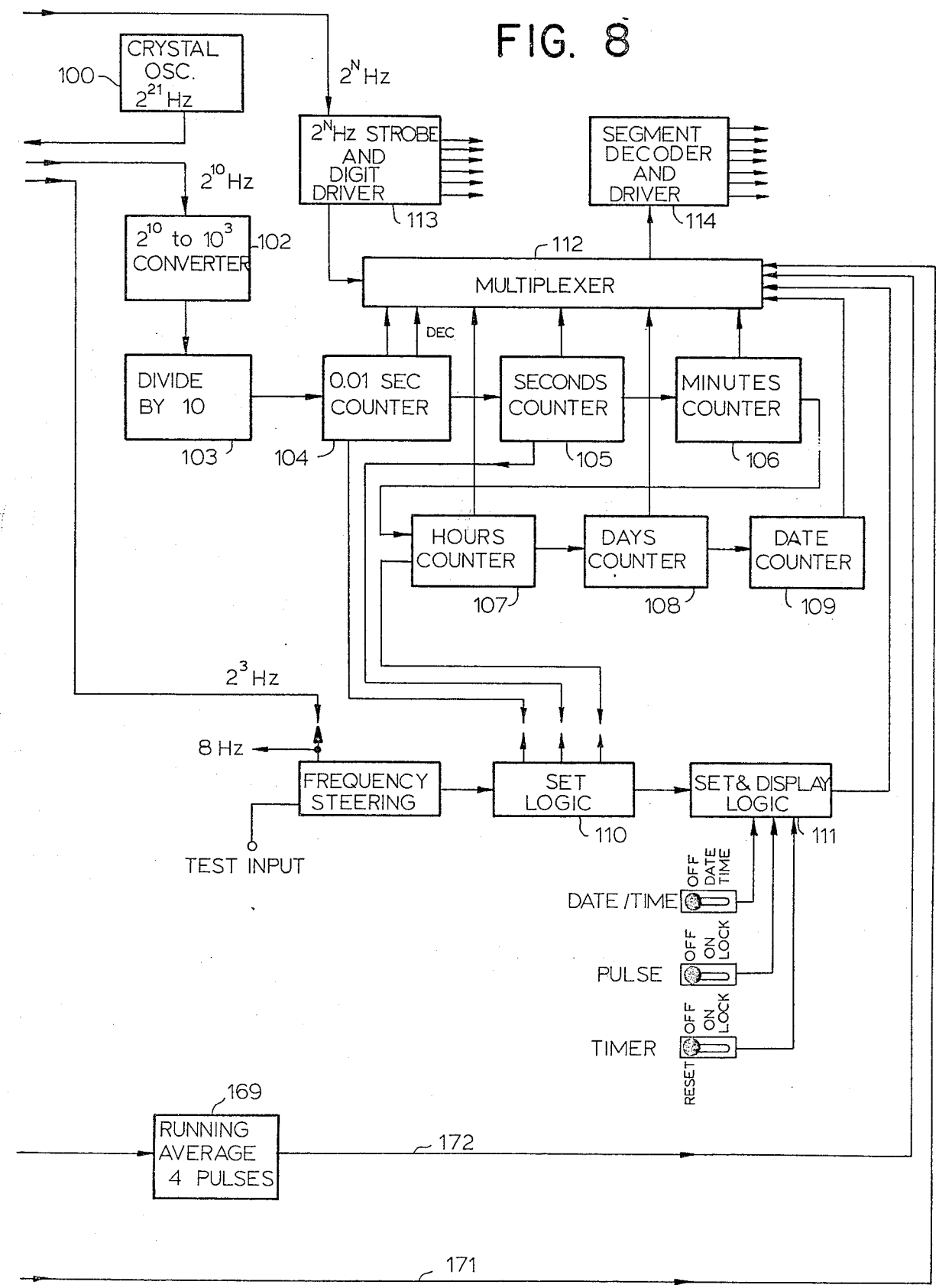

WRIST BORNE PULSE METER/CHRONOMETER

BACKGROUND OF THE INVENTION

For many years both health care professionals and athletic coaches have recognized that the pulse rate of an individual is a primary source of information about the current and long-term condition of a person's physiology. To the health care professional the measurement of pulse rate is a primary measurement taken at the outset of an examination and is a parameter which is measured regularly for continuing diagnosis and care. Hospitals are now well equipped for continuous monitoring of the pulse rate of patients in cardiac and critical care units. To the athletic coach and to the occasional and regular athlete, the pulse rate of the athlete is important and hopefully known. In the past attempts have been made to produce a portable pulse rate meter which can be carried by or worn by the athlete to provide current pulse rate information while the athlete is engaged in strenuous activity such as running. Examples of patents showing pulse rate meters to be worn or carried by individuals are U.S. Pat. Nos. 3,978,849 to Harold S. Geneen, 4,009,708 to John J. Fay, Jr., 4,058,118 to Lawrence J. Stupay et al, 4,030,483 to Jack B. Stevens, 4,063,551 to James Sweeney, and 4,038,976 to Frank M. Hardy et al.

Numerous other patents have issued to inventors of complex pulse rate meters designed for non-portable hospital and other fixed installation use. Examples of such equipment are shown in U.S. Pat. Nos. 4,022,192 to Laukren and 4,018,219 to Hajaiban.

Numerous patents have issued on digital watches and various timing and display circuitry therefor.

Nowhere in the prior art has it been recognized that by combining a pulse rate meter with a digital watch, in addition to the normal advantages one might expect, the resulting instrument has greater contribution than the sum of its parts. It is believed that in the prior art no one has combined a watch giving real time with a pulse-rate meter. And more particularly, no one has used such a combination in which the precise accurate timing circuitry of the watch is used to provide both timing for the signal processing and display of pulse information. The additional accuracy possible allows the display of instantaneous pulse rate on a pulse by pulse basis unrecognized in the prior art. Further, the prior art does not recognize that by the simultaneous display of average and instantaneous values of the wearer's pulse rate, the comparison between instantaneous and average pulse rate may be accomplished to give a direct indication of abnormalities, and the exact time of the abnormality occurrence may be observed.

BRIEF DESCRIPTION OF THE INVENTION

We have discovered that greatly enhanced utility for wrist-borne pulse rate meters is possible by combining the available technology in digital watches with improved signal processing to detect the actual instantaneous pulse rate of the wearer on a pulse by pulse basis, and to simultaneously calculate and display the average pulse rate over a period of time equal to "N" pulses. Thus employing our invention the wearer is able to simultaneously observe his average pulse rate and the last pulse rate. This allows the wearer to follow the cardiac response to changing work loads and to detect abnormalities in his pulse rate which otherwise would be submerged in averaging type circuitry. A simultaneous display of average and instantaneous pulse rate may show a difference between the two which is of no significance, for example by movement of the sensor on the skin or other external interference. On the other hand the display of instantaneous rate may indicate the existence of premature ventrical contractions of the heart requiring the attention of the wearer's physician. The availability of actual time data allows the wearer to know when deviations occurred and this can be calibrated with the nature of his activity, the extent of exertion and physical location if later desired. In accordance with our invention there is the elimination of ambiguity present in many of the types of digital displays where the common field is used to display sequentially data of a different nature requiring the user to first ascertain what data is being displayed followed by an observation and analysis of the data. The data may have changed between the time that the first appraisal is made and the second observation, resulting in a confusing situation.

In accordance with this invention a device which has the general appearance of a digital watch is employed. On the outer face there are a pair of windows. One window displays real time in accordance with common practice for digital watches. The second window, having six digits for data presentation, allocates three spaces to average pulse value and three spaces to the instantaneous pulse value. Selector switches, one for the time record, and the other for the pulse display, are located in the edge of the watch case for easy access. They are of different shape and location to allow tactile identification.

The under face of the case includes a pulse transducer. In one embodiment the pulse transducer is an electro-mechanical device such as a piezoelectric crystal. When the transducer is an electro-mechanical device, the watch must be worn on the volar surface of the wrist but lateral to the tendon cord bundles. In the sub pollex depression, the pulse of the radial artery may be obtained. The ulnar pulse may be obtained on the opposite side of the tendon cord bundle from the radial artery.

In the preferred embodiment the pulse transducer is a light source such as an LED centrally located and encircled by a light detector such as a photo diode. A pair of light blocking rings integral with a lower case face isolate the photo detector from direct view from the light source and from view of the ambient light when the lower face is in contact with the wearer's body e.g. the wrist. In the employment of the light backscatter sensing described above, the watch is worn on the lateral surface of the wrist so that the sensors can respond to the pulse induced changes in the arteriolar and capillary beds in the subcutaneous tissues.

The circuitry accomplishing the improved results of this invention employs a common oscillator which is used to drive both the timing circuitry and display circuitry. The timing circuitry for the watch constitutes well known dividers, counters, a multiplexer and driving circuitry. The display similarly is one of the well known types of LED or liquid crystal. This display is commonly found in watches of the digital type.

The pulse signal processing circuitry of this invention is driven by the same oscillator used in the watch timing functions and includes a circuitry for developing a trigger signal for each pulse of the wearer and for converting the train of clock beats into a stored frequency count in pulses per minute. The last read pulse rate is stored and the values of the last "N" pulse rates are stored. The last pulse rate is displayed via the multiplexer and display. The average of the last "N" rates is determined via a divide by "N" circuit and is likewise displayed via the multiplexer and the display.

Where six digits of time information are desired for example, hour, minutes and seconds, six-digit display is used for time. Employing this invention six digits are required for a display of average and instantaneous pulse rates. Thus two identical six-digit displays are employed in this invention. The time functions are presented in a 3×2 digital display and the pulse rates are presented in a 2×3 digital display.

A novel infra-red source-detector combination is disclosed employing a concentric arrangement of light source and detector and light blocking bosses surrounding each.

BRIEF DESCRIPTION OF THE DRAWING

FIG. 1 is a front face view of the combined digital watch and pulse rate meter of this invention with the straps shown in fragmentary form;

FIG. 2 is a rear view of the invention of FIG. 1;

FIG. 3 is a side elevational view thereof;

FIG. 4 is a rear face view of an alternate embodiment of this invention;

FIG. 5 is a side elevational view of the alternate embodiment of FIG. 4;

FIG. 6 is a fragmentary sectional view of the sensor portion of the embodiment of FIGS. 1 through 3 taken along line 6—6 of FIG. 2;

FIGS. 7 and 8 constitute a block diagram of the circuitry of this invention; and FIG. 9 is a layout diagram for FIGS. 7 and 8.

DETAILED DESCRIPTION OF THE INVENTION

Figure 7:
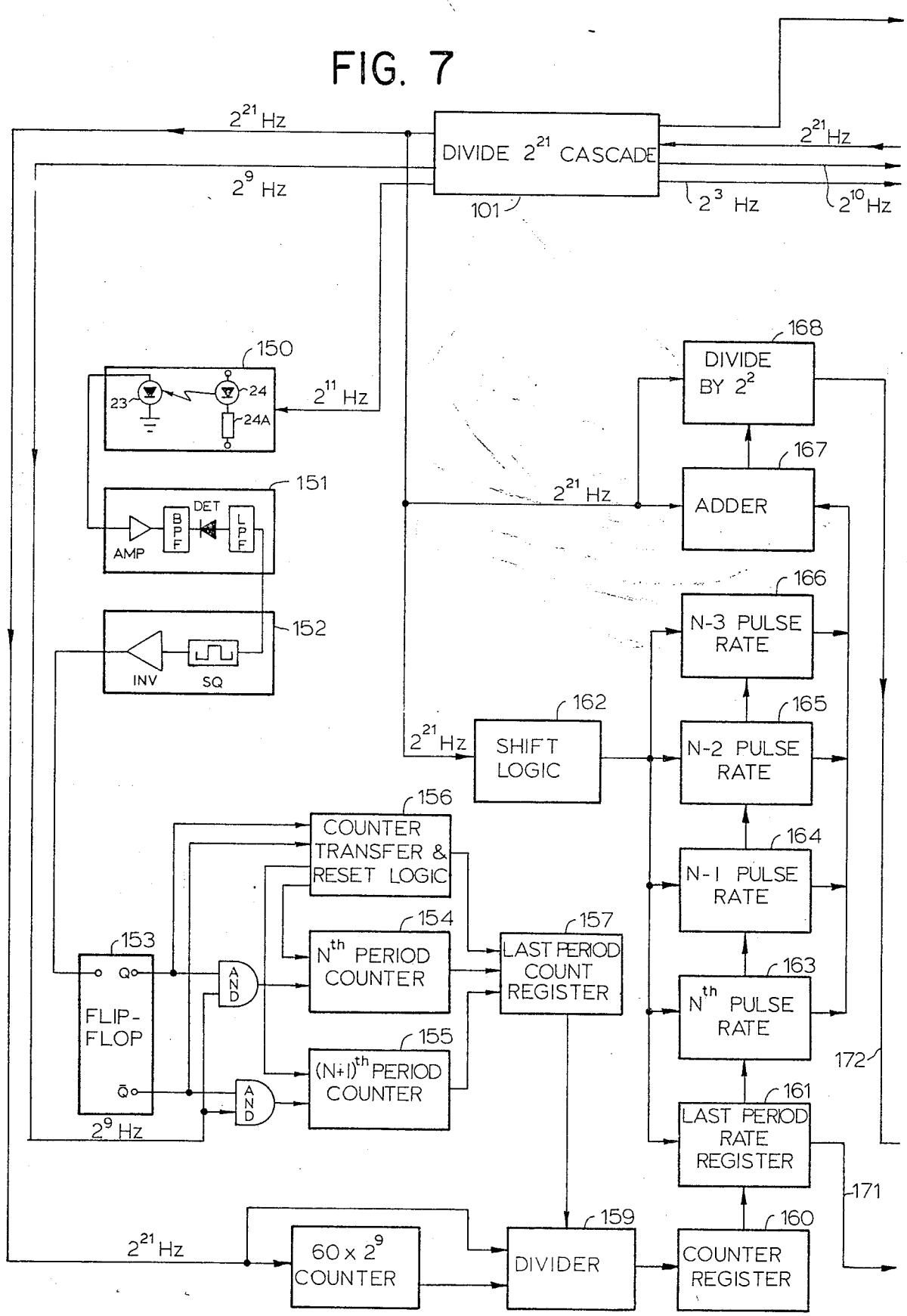

This invention is embodied in a combination wristwatch pulse rate meter in the form best seen in FIG. 1. There, the combination of this invention generally designated 10 is all enclosed within a watch type case 11 having a front face region 12 with a pair of windows 13 and 14. Each of the windows 13 and 14 contain display means, for example, LED, liquid crystal, or other type of visual display commonly used in digital watches. In the preferred embodiment each have a six-digit display which may be similar for purposes of minimization of types of parts utilized in the manufacture. Since it is preferred that the time display has multiple selectable time displays—typical labeling under the time displays is as disclosed. The time functions preferred to be available on demand include:

Date—Day and hour

Hours, Minutes, Seconds and elapsed time

Minutes, Seconds, 0.01 seconds.

In the window 14 again a six-digit display is used but in this case the first three digits display the average pulse rate and the legend indicating the average is located on the front face 12 below the window 14, more particularly below the first three digits space, and the last three digits display the instantaneous pulse rate and is so identified by legend on the face 12. The use of two separate displays is advantageous in that it presents the actual time of the reading and less confusing readout, particularly for the jogger or one who is wearing this invention for medical reasons. Time always appears in one window and pulse rate in the other.

In FIG. 1 the time is registered as 7 hours, 30 minutes and 0 seconds while a typical pulse rate for one engaged in athletic activity is displayed in the lower window 14. The instrument 10 registers an average rate of 122 pulses per minute with an instantaneous or last pulse at a rate of 119 pulses per minute.

In addition to the desirability of dual independent space for time and pulse information, simultaneous display of average pulse rates and instantaneous pulse rate is of significant importance. Prior art pulse rate meters using less precise circuitry employ averaging to avoid displaying an abnormality related to either patient movement relative to the transducer or errors in signal processing. In accordance with this invention, the simultaneous display of average and instantaneous pulse rate provides three important sets of information; the two values displayed plus the simultaneous comparson of the two. The average pulse rate is important in showing the trend over a number of cycles and will tend to change less dramatically. Thus a jogger can watch his pulse climb from start of activity towards the limit he or his doctor has set.

Any abnormality in any one pulse is clearly displayed in the right three digits of the pulse rate display. Its displacement from the average rate indicates the abnormality to the wearer at the same instant he is observing the average rate. The abnormality may indicate a premature ventricular contraction of the heart about which the wearer should be concerned based upon his doctor's evaluation, or it may be due to some abnormality of movement of the watch on the wrist or due to some abrupt change in the activity of the user.

Thus, the average value and the instantaneous value both bear significant information and the comparison of the two values made possible by this simultaneous display in the same window provides additional significant information to the wearer. The time display is simultaneously available. Thus, time of occurrence is observable as well.

The combination of this invention preferably includes three controls—15, 16, and 17 as follows:

|  |  | Function | Positions |
|---|---|---|---|
| Watch | Switch 15 | Date or time selection | Display off<br>Date on<br>Time on |
| Pulse Rate | Switch 16 | Pulse Sensor and Display Condition | (1) Sensor and Display OFF<br>(2) Sensor and Display ON<br>(3) Sensor OFF Display locked |
| Timer or Stop Watch | Switch 17 | Control Stop Watch Timer and Display | (1) Timer OFF/Reset Display OFF<br>(2) Timer ON Display ON<br>(3) Timer OFF Display Locked ON to fast recording. |

The timer function is useful particularly for one doing timed exercises or jogging but is not mandatory. It employs the accurate timing circuitry of the watch and uses its display as well. To aid in eliminating any ambiguity in the nature of the reading, the timer switch 17 further produces the display of a decimal point ahead of the hundredths position. This signal plus the rapid change of the last two positions (hundredths of a second) gives the user a clear indication that the timer fraction is being displayed in the time window 13.

Switch 15 will have three fixed positions to select the time function display mode and pulse mode for setting or adjusting time functions.

The combination 10 is held on the wearer's body by a pair of straps 20 and 21 which may be ordinary watch straps in the preferred embodiment of this invention since all powering, sensing and control features of this invention are contained within the case 11.

Now referring to FIGS. 2–5, which are side and under side views of the invention of FIG. 1, the typical relationship of the straps 20 and 21 to the case 11 are more clearly apparent, and in these views the transducer portion on the underside of the case 11 may be seen. This transducer structure is contained within a boss region 22 of substantial diameter in order to provide a relatively large area of intimate contact with the user's wrist. This will insure both comfortable wearing and sufficient contact for obtaining an accurate pulse indication by either a pulse transducer of the pressure type contained therein shown in FIGS. 4 and 5, or by the preferred embodiment employing an infra-red source-detector combination as best shown in FIG. 2.

Watch straps must provide adjustable tension in as much as the sensors must be forced into the flesh of the wrist for a reading. This situation may be uncomfortable over a prolonged period of time and the strap may include provision for release of pressure during normal wearing.

A suitable detector is the type CLT 2160 photo diode produced by Clairex Electronics, Inc., of Mount Vernon, New York 10550.

Centrally located within the detector 23 is a secondary boss 22A, and an infra-red source 24 which may, for example, be a light emitting diode such as type SSL 55 CF of the General Electric Company, which provides emissions in the near infra-red region.

The circular detector array 23 surrounding the infra red source 24 insures a detection of the change in optical backscatter of the subcutaneous arteriolar and capillary bed of the wearer with each heart contraction and resultant pulse of oxygenated blood. The boss 22 serves to isolate the infra-red detector from ambient light. The boss 22A prevents direct transmission of light between source 24 and detectors 23. The coaxial arrangement of these three elements provides a relatively large contact surface area resulting in not only effective sensing of a pulse rate but minimum discomfort to the wearer. The circular array of the detector 23 allows the detection of pulses in a substantial arteriolar-capillary bed within the hemispherical region denoted in FIG. 6 for increased signal to noise ratio and energy utilization. In FIG. 3 in partial cross-section, two sections of a single circular apertured disc photo-detector, 23a, are shown. The single photo-detector 23a, or the circular array 23 of FIG. 2 allows integration of the backscatter field which serves the dual purpose of increasing signal sensitivity and reducing position dependence of the pulse meter.

An alternate, less preferred transducer is illustrated in FIGS. 4 and 5. There boss 32, similar to boss 22, is present however, a pressure transducer 33 constitutes the pulse source in direct contact with the wrist of the wearer. The transducer 32 may be of the piezoelectric or other type well known in the art.

DESCRIPTION OF THE CIRCUITRY

The circuitry of this invention which provides for the combinatiion of time, average pulse rate and instantaneous pulse rate information is represented in accordance with the preferred circuitry as shown in block diagram form in FIGS. 7 and 8.

Now referring to FIGS. 7 and 8 in conjunction with FIGS. 1 through 6 for reference, the basic timing element of this invention is an oscillator 100, for example a crystal oscillator operating at a suitable frequency, for example $2^{21}$ Hz. There are precision oscillator crystals mass produced for watch circuits with nominal frequencies of $2^{15}$ Hz and at $2^{16}$ Hz. The $2^{15}$ Hz is too slow for both precision timing and computation storage and and is based upon every pulse period. The $2^{16}$ Hz is marginal. The $2^{21}$ Hz is also a mass produced, precision crystal which may be economically employed. At this frequency there is ample speed to execute all of the timing, storage, computational, transfer and display functions. The output of the oscillator 100 is introduced into the cascaded divider network 101 constituting a plurality of divider steps so arranged to provide sub-multiples of the basic frequency. Typical frequencies of the divider 101 used are $2^{10}$ Hz used to control the chronometric measurements, $2^3$ Hz used to control frequency steering logic and display logic; $2^9$ Hz for use in the pulse signal acquisition and processing circuit and $2^{21}$ Hz used in the processing storage and computing of pulse-rates.

The $2^{10}$ Hz signal from the divider 101 is itself introduced in two series connected converters or dividers 102 and 103; the former, converting the $2^{10}$ Hz signal to the train of pulses of one millisecond duration, and the divider 103 providing 0.01 second timing pulses which are used to drive a hundredth of a second counter 104. The 0.01 second counter 104 is in actuality two cascaded decade counters. Upon overflow after a count of 99 this counter 104 automatically resets to a count of 00.

The seconds counter 105 is actually two decade counters set to overflow and reset to 00 after reaching a count of 59. At each overflow and reset a pulse is sent to the minutes counter 106. Thus counter 104 produces an output pulse to a seconds counter 105 every 100 pulses constituting one second. The seconds counter 105 in turn produces one output pulse to a minutes counter 106 every sixty seconds. The second counter 105 is actually two decade counters set to overflow and reset to 00 after reaching a count of 59. At each overflow and reset, a pulse is sent to the minutes counter 106. The minutes counter in turn produces an output pulse each sixty counts to an hours counter 107. The hours counter 107 produces a single output pulse to a day counter 108 once each 24 hours. The day counter 108 in turn produces an output pulse for each pulse, and this latter pulse is introduced into the date counter 109 which in turn provides output pulses once each day to the multiplexer 112. The display elements must be presented at a rate faster than the normal human flicker perception which is approximately 16 Hz, or $2^4$ Hz. Digital displays at 64 Hz are perceived as a steady source. Strobe pulses for the multiplexer 112 are provided by a $2^n$ Hz strobe and digit driver circuit 113 which is additionally connected to a strobe source for the display if required. The multiplexer 112 provides the output of the stored information introduced by each time function source from 1/100th seconds through the date counter to the segment decoder and segment driver circuit 114 which is directly connected to the date time display in windows 114 in FIG. 1. Each of the foregoing aspects of the chronometry circuitry is well known in the digital watch field and a mre complete understanding of the selection and operation of such circuitry may be had by reference to a number of prior patents or publications but particularly the article entitled "An I²L Watch Chip with Direct LED Drive" article entitled ("An I² Watch Chip with Direct LED Drive") appearing in the Journal of Solid State Circuits, Vol. SC-11 No. 6, December 1976 at Page 847 et seq by Patrick A. Tucci and Louis K. Russell.

PULSE METER

The pulse measuring portions of this invention are all driven by the same basic oscillator 100 which drives the chronometric system. The basic timing frequency from the crystal oscillator 100 has been divided into sub-multiple frequencies $2^9$ Hz, $2^{11}$ Hz, and $2^{21}$ Hz in the divider 101 and are used in the pulse signal portions of the invention.

Signal acquisition employing our preferred embodiment is accomplished in the block identified as 150, Signal Acquisition. It includes the infra-red signal source 24 which optionally, in order to save power, may be pulsed under the control of a pulse power source, 24A. Typically, a duty cycle of 20 percent is suitable at a pulse rate of 2 KHz.

The infra-red detector 23 will detect the backscatter signal emanating from the wrist of the body portion of the wearer in the form of a 2 KHz signal modulated in amplitude at the pulse rate of the individual. This signal is then passed through a suitable amplifier having gain, for example of 1000, and through a band pass filter BPF typically having a pass band of 1000 Hz centered at 2 KHz. The signal is then envelope detected in a suitable detector to provide the pulse wave and filtered through a low pass filter having a cutoff in the order of 10 Hz to eliminate such interference as 60 cycle hum or other higher frequency signals that might be picked up. The detected filtered pulse signal is then introduced into signal conversion circuit 152 which typically includes a pulse square and inverter to provide an output square wave at the frequency of the wearer's pulse. This signal is then introduced as the switching signal to a bi-stable multivibrator 153 having a pair of AND gates, each having one input coupled to output leads of opposite states of the multivibrator 153. The second input to each AND gate is a timing signal at a $2^9$ Hz frequency. Each of these AND gates will pass the $2^9$ Hz signals to their respective counter 154 and 155 for the period that the multivibrator 153 is in an ON state associated with that particular AND gate. The counter 154 termed the Nth period counter, stores the number of $2^9$ Hz pulses which pass through its associated AND gate. Similarly, the counter 155 which is identified as Nth+1 period counter, stores the number of $2^N$ Hz pulses passing through its associated AND gate when enabled. When there is no change in the pulse rate between two successive individual pulses of the wearer, the count in both counters 154 and 155 will be identical. As the pulse rate of the wearer changes, the count in the counters 154 and 155 will each change accordingly. The change from pulse rate from counter period to counter period reflects the wearer's change in pulse rate on a per pulse basis.

Both the counters 154 and 155 are under the control of a counter transfer and reset logic circuit 156, which is itself under the control of flip-flop 153. As each counter is loaded via its respective AND gate and the flip-flop switches to the opposite state, a dump signal is received from the transferred logic circuit 156 followed by reset applied to that particular counter. The count in each counter is sequentially introduced into the last period counter register -157, itself controlled by the logic circuit 156. The count in register 157 is introduced into a divider 159 immediately before reloading. In the divider 159, the count present in the register 157 is divided into the constant $60\times2^9$ from counter 168. The output of the divider 159 is the rate in pulses per minute. It is introduced into counter register 160 and in turn introduced into last pulse rate register 161 where the last pulse rate in pulse per minute is temporarily stored. Output lead 171 from the register 161 is used to convey that last pulse rate signal to multiplexer 112 where it is in turn applied to the instantaneous pulse display. In addition to the register 161, there are four storage registers 163 through 166, each of which store the last four sequential pulse rates with the transfer of pulse rates between the stages 161 through 166 under the control of shift logic circuit 162. The total number of pulses in the registers 163 through 166 is obtained in adder 167. By dividing by $2^2$ in divider 168, the number of storage registers 163 through 167, the average pulse rate for the last four pulses is obtained and introduced via lead 172 after passing through an average count register 169. The running average on lead 172 is also introduced into the multiplexer 112 for display in the average pulse position digits of display 14 of FIG. 1.

What is claimed is:

1. A combined digital watch and pulse rate meter comprising:
   a case having an upper face and a lower face;
   the upper face including display means for display in digital form time of any information;
   said display further including means for displaying the six digits of pulse information;
   a timing signal generator within said case;
   timing circuitry coupled to said timing signal generator for deriving fractions of seconds, seconds and minutes information;
   means for displaying said time information on said display;
   a transducer on the inner face of said case positionable in pulse sensing relationship with the wearer;
   said transducer coupled to signal processing circuitry for deriving the pulse rate of the wearer;
   said signal processing circuitry coupled to said timing signal generator to provide a time base for pulse measurement accuracy equal to the accuracy of the time of day signal;
   means for coupling pulse information from said signal processing circuitry to three digits of said display on a pulse by pulse basis to provide instantaneous pulse rate display;
   means for storing the last "N" pulse rates detected;
   means for averaging the last "N" pulse rates stored; and
   means for coupling the average pulse rate to the last set of three digits of said display whereby the pulse rate average is displayed for the wearer.

2. The combination in accordance with claim 1 wherein said display means comprise a pair of six digit decimal displays whereby time and pulse information may be simultaneously displayed for continuous comparison by the wearer.

3. The combination in accordance with claim 2 wherein said pulse rate display is controlled and enabled by a single switch means whereby average and instantaneous pulse rate values are simultaneously displayed.

4. The combination in accordance with claim 1 wherein "N" is four.

5. A combined digital watch and pulse rate meter comprising:

a case having an upper and a lower face;

the upper face including digital display means for displaying time information;

said display means including means for displaying six digits of pulse information;

a timing signal generator within said case;

timing circuitry coupled to said timing signal generator for deriving fraction of seconds, seconds and minutes information;

means for displaying said time information on said display;

a transducer on the inner face of said case positionable in pulse sensing relationship with the wearer;

said transducer coupled to signal processing circuitry for deriving the pulse rate of the wearer;

said signal processing circuitry coupled to said timing signal generator to provide a time base for pulse measurement accuracy equal to the accuracy of the time signal;

means for coupling pulse information from said signal processing circuitry to three digits of said display on a pulse by pulse basis to provide instantaneous pulse rate display;

means for storing the last "N" pulse rates detected;

means for averaging the last "N" pulse rates stored;

means for coupling the average pulse rate to the last set of three digits of said display whereby the pulse rate average is displayed for the wearer;

wherein said signal transducer comprises a light source having a frequency distribution including the 900 nanometer range positioned at a central location in the rear face of the case;

photodetector means positioned radially around said light emitting source;

first light obstructing means preventing direct illumination of said photo detector means by said light source;

second light obstructing means shielding said photo detector means from external sources when the lower face of said case is maintained in contact with the skin of the wearer;

wherein said first and second light obstructing means comprise a pair of annular rings extending above the surface of the lower face of said case whereby said rings are in contact with the skin of the wearer and light transmission to said detector is limited to light emanating from the skin of the wearer.

6. The combination in accordance with claim 5 wherein said light detector comprises a continuous ring detector located between the first and second light obstructing rings.

7. The combination in accordance with claim 6 wherein said light source comprises a light emitting diode.

8. The combination in accordance with claim 6 wherein said light detector comprises a photo diode.

9. A pulse rate meter to be worn by a user comprising;

A case;

means holding one side of said case against the wearers body;

said case enclosing (a) a timing signal source;

(b) a sensor in pulse sensing relationship with the wearer for producing an electrical signal for each pulse of the user;

(c) means for converting the pulse rate of the user into a train of timing signals, the number of which define the pulse period for each pulse period of the user;

(d) two counting means;

(e) means coupling trains of timing signals in alternate sequential order to said two counting means;

(f) a register;

(g) control means for alternately introducing the count of said two counting means into said register and for resetting said counting means;

(h) means for converting the count from said register into the wearer's pulse rate;

(i) a display means on an outer wall of said case;

(j) means for applying the output of said converting means to said display to display the user's pulse rate for the last pulse;

(k) means for storing "N" signals representative of "N" pulse rates measured;

(l) means for averaging said "N" pulse rates measured; and (m) means for applying the output of said averaging means to said display means whereby both the instantaneous and average pulse rates are available to the user by observation of the display on said case wall.

10. The combination in accordance with claim 9 wherein said display includes sufficient digits to display both average and instantaneous pulse rates simultaneously and said instantaneous and average pulse rates are applied simultaneously thereto.

11. The combination in accordance with claim 9 wherein said number "N" is four.

12. The combination in accordance with claim 9 including "N" storage registers coupled to said converting means in service whereby each of the last "N" pulse rates is stored in sequence, said averaging means operative to average the last "N" pulse rates and whereby a running average of "N" pulse rates is displayed.

13. The combination in accordance with claim 9 including clock means for timing seconds, minutes and hours;

said display means coupled to said clock means including means for displaying seconds, minutes and hours as determined by said clock means;

said pulse meter and clock means both employing said timing signal source.

14. The combination in accordance with claim 9 including an elapsed time measuring circuit;

said display means coupled to said elapsed time measuring circuit;

said pulse meter and elapsed time measuring circuit both employing said timing signal source.

15. An improved pulse rate meter comprising:

a housing including an upper face and a lower face;

display means on said upper face for displaying pulse rate information;

sensor means on said lower face for sensing the wearer's pulse rate;

means securing said housing to the wearer with the lower face in contact with the wearer's skin;

said sensor means comprising a source of radiant energy;

at least one radiant energy detector laterally displaced on said lower face of said housing from said source of radiant energy;

means on said lower face for blocking direct radiation from said source of radiant energy to said detector;

second means on said lower means for blocking radiant energy to said detector from said radiant energy source except that reradiating from the skin of the wearer;

wherein said first and second radiant energy blocking means comprises a pair of concentric raised bosses on the lower face of said housing.

* * * * *